(12) United States Patent
Nakamura et al.

(10) Patent No.: US 8,022,191 B2
(45) Date of Patent: Sep. 20, 2011

(54) PEG-CONJUGATED ERYTHROPOIETIN

(75) Inventors: Teruo Nakamura, Shizuoka (JP); Yasuo Sekimori, Shizuoka (JP); Minoru Machida, Shizuoka (JP); Hiromitsu Kawata, Shizuoka (JP); Hajime Miyamoto, Shizuoka (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/498,053

(22) Filed: Aug. 3, 2006

(65) Prior Publication Data
US 2006/0276634 A1 Dec. 7, 2006

Related U.S. Application Data

(62) Division of application No. 10/399,254, filed as application No. PCT/JP01/08539 on Sep. 28, 2001, now abandoned.

(30) Foreign Application Priority Data

Oct. 16, 2000 (JP) .................................. 2000-315421

(51) Int. Cl.
*A61K 38/18* (2006.01)
(52) U.S. Cl. .......... 530/399; 530/402; 530/412; 514/7.7
(58) Field of Classification Search .................. None
See application file for complete search history.

(56) References Cited

U.S. PATENT DOCUMENTS

| 4,179,337 A | 12/1979 | Davis et al. |
| 4,904,584 A | 2/1990 | Shaw |
| 5,100,664 A * | 3/1992 | Doyle et al. ................. 424/85.2 |
| 5,747,446 A * | 5/1998 | Sytkowski ........................ 514/8 |
| 5,767,078 A | 6/1998 | Johnson et al. |
| 5,824,784 A | 10/1998 | Kinstler et al. |
| 6,583,272 B1 | 6/2003 | Bailon |

FOREIGN PATENT DOCUMENTS

| EP | 0 605 963 | 7/1994 |
| EP | 1 064 951 | 1/2001 |
| JP | 2-9900 | 1/1990 |
| JP | 2-502646 | 8/1990 |
| JP | 9-25298 | 1/1997 |
| WO | WO 95/06058 | 3/1995 |
| WO | WO 96/28475 | 9/1996 |
| WO | WO 98/32466 A | 7/1998 |
| WO | WO 99/03887 A | 1/1999 |
| WO | WO 00/32772 A | 6/2000 |
| WO | WO 00/42175 A | 7/2000 |
| WO | WO 00/44785 | 8/2000 |
| WO | WO 01/02017 A | 1/2001 |

OTHER PUBLICATIONS

Bailon et al., "Polyethylene Glycol-Conjugated Pharmaceutical Proteins", *PSTT*, 1(8):352-356 (1998).
Francis G E et al "Pegylation of Cytokines and other Therapeutic Proteins and Peptides: The Importance of Biological Optimisation of Coupling Techniques" International Journal of Hematology, Elsevier Science Publishers, vol. 68, No. 1, Jul. 1998, pp. 1-18.
Jubinsky et al., "The β Chain of the Interleukin-3 Receptor Functionally Associates With the Erythropoietin Receptor", *Blood*, 90(5):1867-1873, (1997).
Malik F et al "Peg-modified erythropoietin with improved efficacy" Experimental Hematology, New York, NY, USA, vol. 28, No. 7, Jul. 2000 p. 106.
Malik F et al "Polyethylene Glycol (PEG) Modified Erythropoietin: A Second Generation Cytokine" Experimental Hematology, New York NY USA. vol. 23, No. 8, Aug. 1995 p. 835.
Matthews et al., "A Sequential Dimerization Mechanism for Erythropoietin Receptor Activation", *Proc. Natl. Acad. Sci. USA*, 93:9471-9476, (1996).
Monkarsh SP et al "Positional isomers of monopegylated interferon alpha-2a: isolation, characterization, and biological activity" Analytical Biochemistry, Academic press, San Diego CA USA vol. 247, No. 2. May 1, 1997 pp. 434-440.

\* cited by examiner

*Primary Examiner* — Gyan Chandra
(74) *Attorney, Agent, or Firm* — Browdy and Neimark, PLLC

(57) ABSTRACT

The present invention provides a polyethylene glycol-conjugated erythropoietin (PEG-conjugated EPO) prepared by PEG conjugation on the lysine residue at position 52 of native erythropoietin (native EPO). In order to achieve more sustained efficacy without losing physiological activities of native EPO, a glycoprotein rich in sugar chains, there has been a need to develop a PEG-conjugated EPO with significantly sustained efficacy by introducing a controlled number of PEG molecules at controlled positions. This PEG-conjugated EPO addresses such a need and provides more sustained efficacy.

5 Claims, 13 Drawing Sheets

M E 1 2 R

SDS-PAGE of PEG-conjugated EPOs on 4-15% gradient gel SDS-PAGE.

M: MW marker (53, 76, 116, 170, 212 (kDa))
E : EPO
1 : mono-mPEG-EPO
2 : di-mPEG-EPO
R: Reaction mixture of PEG-conjugated EPOs Figure 6  Time course of peripheral reticulocyte counts

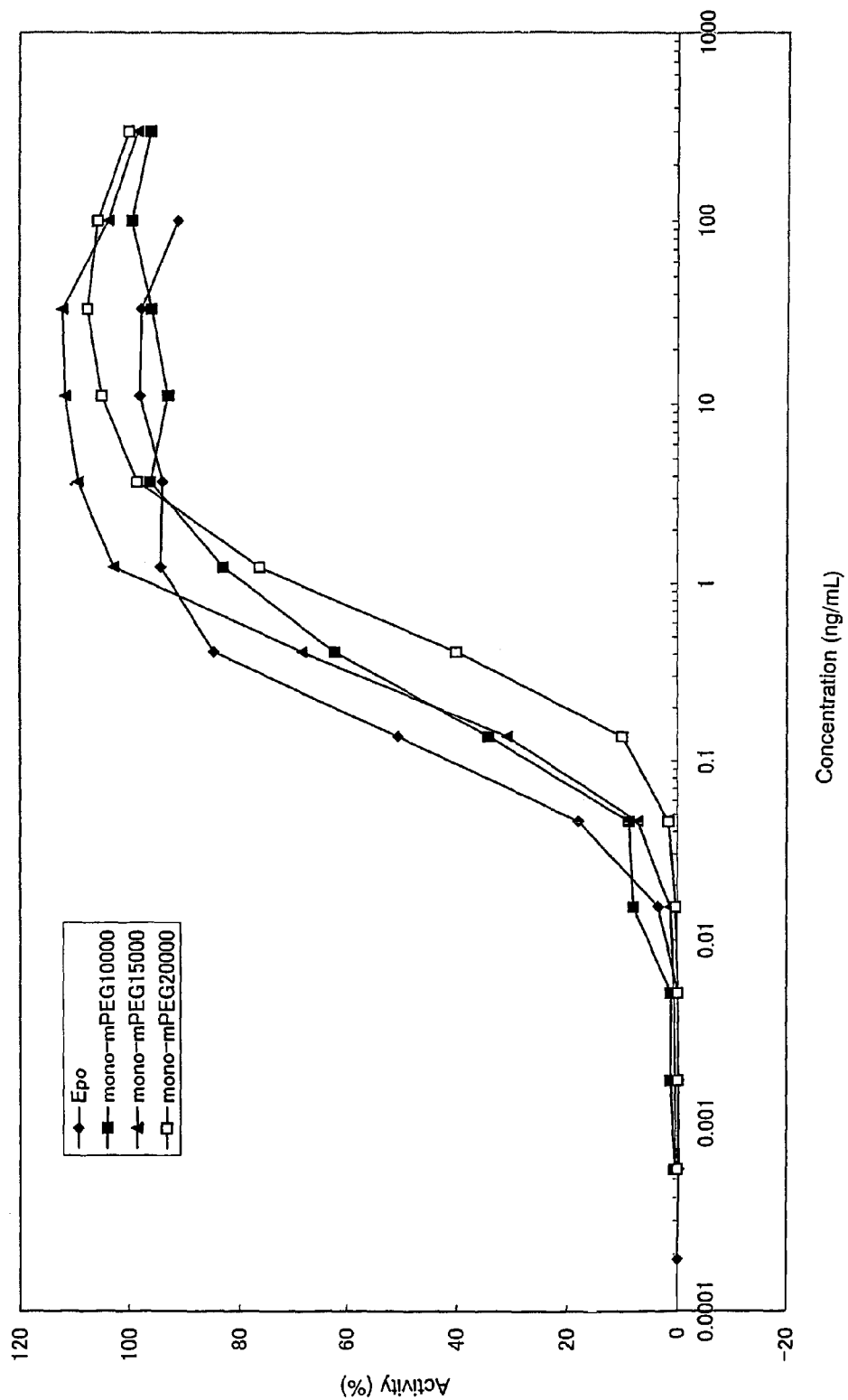
Figure 10  Cell growth activity of PEG-EPOs on BaF/EpoR cells

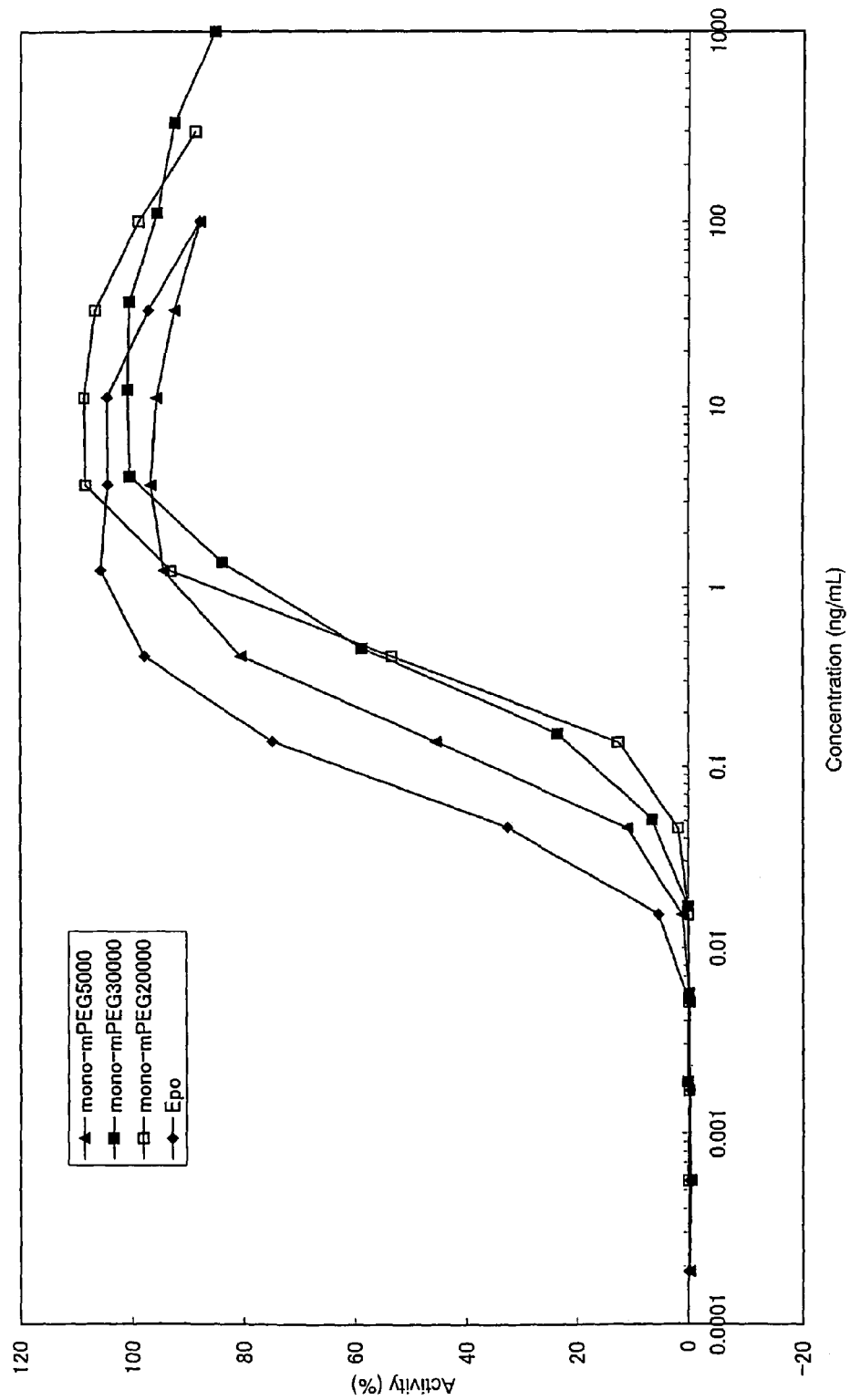
Figure 11 Cell growth activity of PEG-EPOs on BaF/EpoR cells

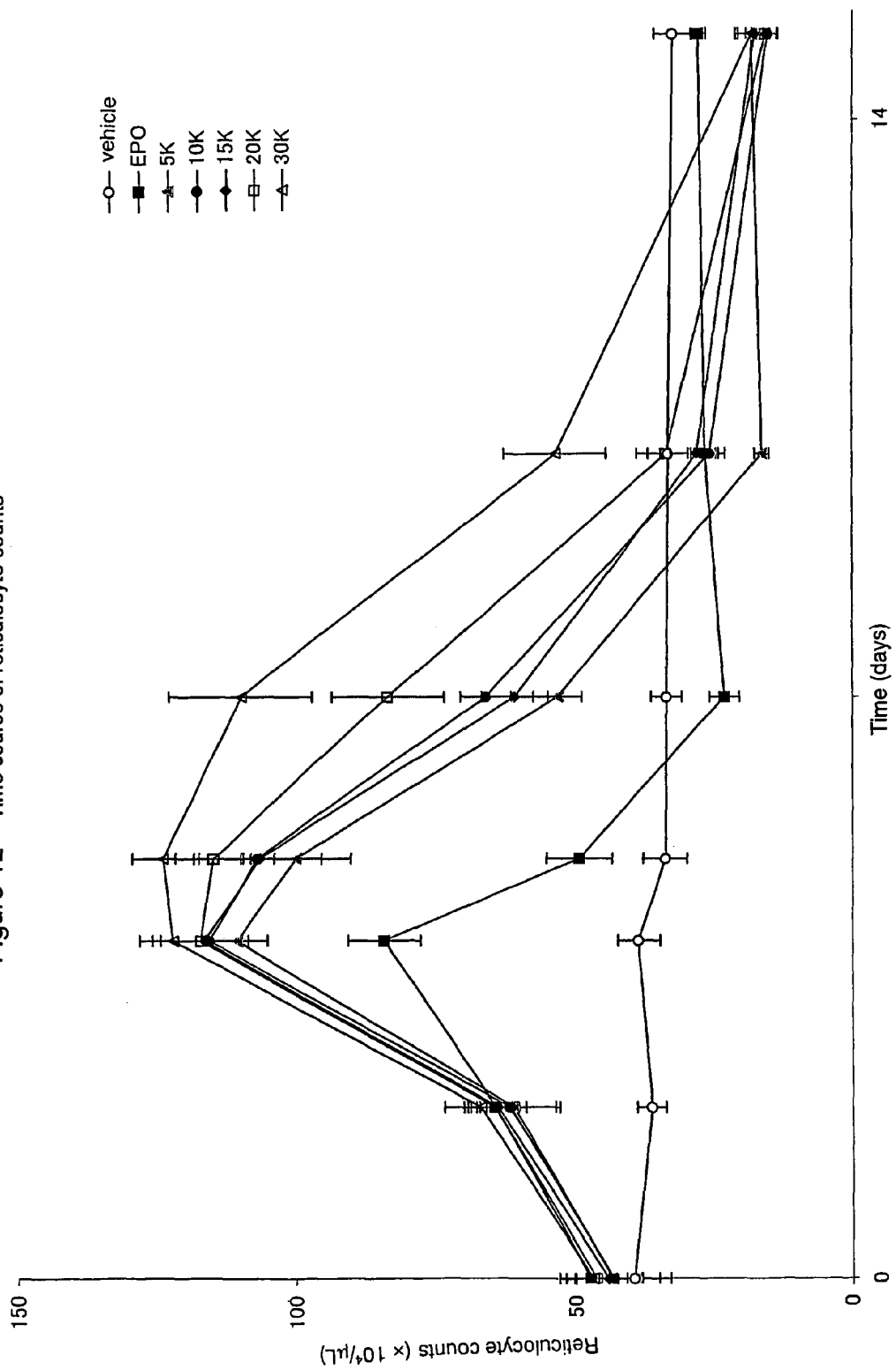
Figure 12  Time course of reticulocyte counts

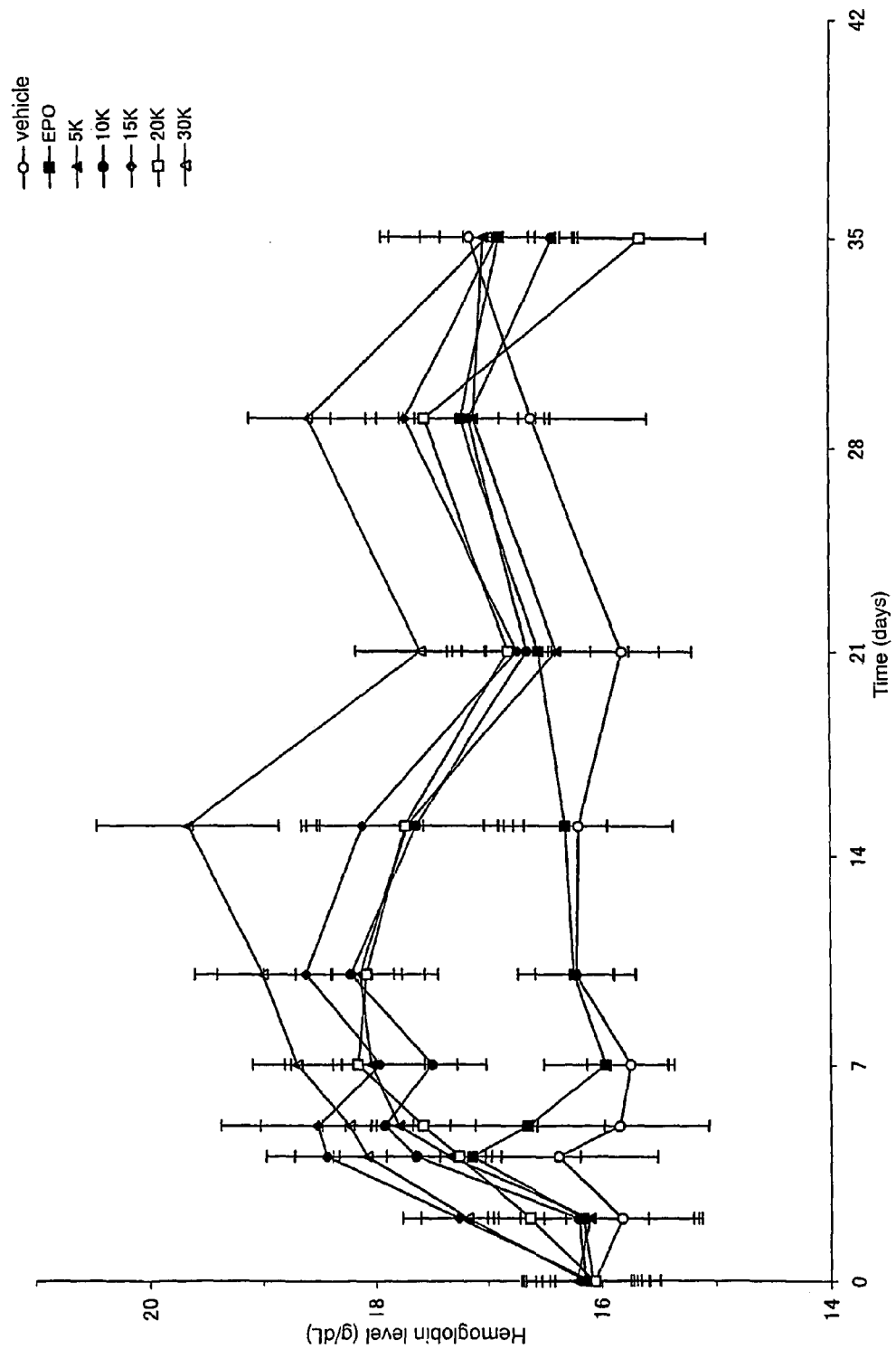

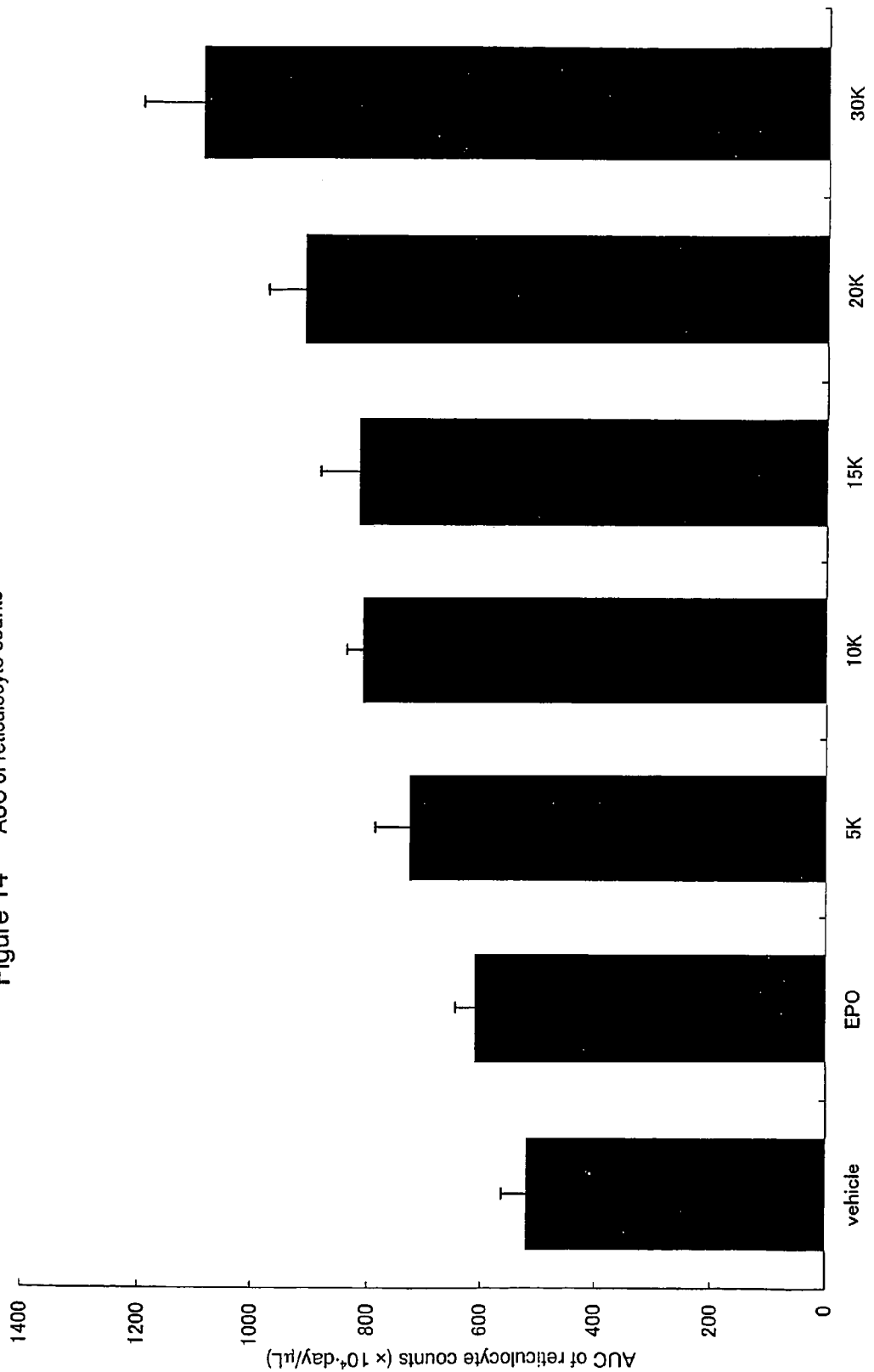

PEG-CONJUGATED ERYTHROPOIETIN

This is a division of application Ser. No. 10/399,254, filed Apr. 16, 2003, which was a §371 of international application, PCT/JP01/08539 filed Sep. 28, 2001, both of which are herein incorporated by reference.

TECHNICAL FIELD

The present invention relates to native human erythropoietin chemically conjugated with polyethylene glycol (PEG). More specifically, the present invention relates to mono-PEG-conjugated erythropoietin having a PEG molecule primarily attached to the lysine residue at position 52, which is obtained by reacting recombinant human erythropoietin (rhEPO) produced in animal host cells with an amino reactive derivative of PEG; a composition comprising the conjugate; and a sustained-action erythropoietin formulation comprising the conjugate or composition as an active ingredient.

BACKGROUND ART

Erythropoietin (EPO) is a polypeptide rich in sugar chains, which is predominantly produced in the kidneys and acts on precursor cells of hematopoietic tissue to stimulate their differentiation and proliferation into erythrocytes. EPO is currently commercially available as human EPO recombinantly produced in animal host cells, and its main use is as a therapeutic agent for various types of anaemia, including renal anemia caused by the underproduction of EPO resulting from nephropathy.

As used herein, the term "native EPO" is intended to encompass human urine-derived EPO, such as those extracted, isolated and purified by various techniques, and recombinant human EPO (rhEPO) having the same sugar chains as human-derived EPO, such as those recombinantly produced in animal host cells (e.g., CHO cells, COS cells), as well as their variants modified to include substitution or deletion of one or more amino acids constituting such EPOs or modified to include addition of one or more amino acids.

Currently used EPO is administered, e.g., by intravenous, subcutaneous or intramuscular route. The percentage of reticulocytes (erythrocyte precursors) in total erythrocytes can be used as an indicator for EPO activity. The activity of native EPO observed as the percentage of reticulocytes will reach a peak 3 to 5 days after administration by any route mentioned above, followed by a rapid decline. Thus, native EPO should be injected twice or three times per week to ensure sufficient therapeutic effects in anaemia patients. This not only causes pain in the patients, but also provides additional load on overworked doctors and other medical staff members. Further, a decreased number of injections required within a fixed period of time will save medical costs.

On the other hand, there are reports on proteins or glycoproteins conjugated with water-soluble polymers (e.g., PEG) having a hydrazide or oxylamine moiety capable of covalent bonding through chemical reaction with an oxidizable functional group such as polyol, lactol, amine, carboxylic acid or a carboxylic acid derivative on the proteins or glycoproteins (see, e.g., JP 7-196925 A). According to this report, a water-soluble polymer, such as PEG, can be attached to various free radicals on amino acids or sugar residues constituting a protein or glycoprotein to yield a coupling product with 6 to 34 PEG molecules (molecular weight: 2000 to 12000) per protein molecule. In such a PEG-conjugated protein or glycoprotein with many PEG molecules, it is difficult to control the positions and number of PEG molecules attached to the protein or glycoprotein and it is hard to obtain an uniform PEG-conjugated protein or glycoprotein. Thus, there is a problem when the PEG-conjugated protein or glycoprotein thus prepared is formulated into pharmaceuticals.

There is also a report disclosing a sulfonate ester-activated polymer (e.g., sulfonate ester-activated PEG) and proposing a method in which this sulfonate ester-activated polymer is reacted with a target material (e.g., a protein or glycoprotein) to prepare a polymer-conjugated target material (see JP 9-504515 A). Examples of a reactive group on a target material which reacts with this sulfonate ester-activated polymer include a primary or secondary amino group, a thiol group and an aromatic hydroxyl group. In such a sulfonate ester-activated polymer capable of reacting with various reactive groups, it is therefore regarded as difficult to control the number and positions of conjugatable polymer molecules which are introduced. Also, such a polymer clearly has the possibility of sulfonate amide formation, which allows much higher heterogeneity for products.

Further, there is a report on a branched polymer (e.g., branched PEG) which is attached to a target material (e.g., a protein or glycoprotein) to give a branched polymer conjugate of the target material (see JP 9-504299 A). Although this branched polymer-conjugated target material also successfully sustains its efficacy, it has been desired to develop polymer-conjugated EPOs with more sustained efficacy.

Also, it has been believed that conjugation with higher molecular weight PEG would result in more sustained efficacy.

Conjugation with higher molecular weight PEG will cause a larger decrease in the in vitro activity of EPO. However, it has been believed that EPO conjugated with higher molecular weight PEG would show significantly improved plasma retention and hence sustained in vivo activity, resulting in greater and more sustained activity with increase in the molecular weight of PEG (Polyethylene glycol-conjugated pharmaceutical proteins; PSTT Vol. 1, No. 8, 1998, 352-356). For example, in the case of a PEG conjugate of G-CSF mutaine, it is known that its in vivo activity increases in proportion to the calculated molecular weight of PEG in the range of about 10 kDa up to 70 kDa (PCT/US00/01264, WO 00/44785).

Conventional PEG conjugates of EPO were designed to have many PEG molecules with a relatively low molecular weight of around 5 kDa in order to sustain their efficacy. However, in EPO rich in sugar chains, conjugation was limited exclusively to unglycosylated amino acid residues involved in receptor binding, making it impossible to avoid a decrease in in vivo activity and difficult to balance sustained efficacy and decreased in vivo activity. Also, even in a case where amino groups or sugar chains are conjugated with PEG of greater than 10 kDa as stated above, there has been a difficulty in practically formulating PEG-conjugated EPO into drugs because the problem of controlling the number of PEG molecules still remains.

DISCLOSURE OF THE INVENTION

For these reasons, in order to achieve more sustained efficacy without losing physiological activities of EPO, a glycoprotein rich in sugar chains, there is a need to develop a PEG-conjugated EPO with significantly sustained efficacy by introducing a controlled number of PEG molecules at controlled positions.

As stated above, the general recognition of the relationship between the molecular weight of PEG used for conjugation and in vivo activity of EPO was that EPO conjugated with higher molecular weight PEG showed more improved plasma retention and hence greater and more sustained efficacy. However, the inventors of the present invention have clarified that such general recognition does not apply to PEG conjugation for native (recombinant) EPO with sugar chains because conjugation with extremely high molecular weight PEG also reduces the in vivo activity of EPO. As a result, they have found that higher molecular weight PEG does not always produce a better result, but rather there is an optimal range for the molecular weight of PEG to have a balance between sustained efficacy and in vivo activity, as well as finding that a particular number of PEG molecules provides the most sustained efficacy. These findings led to the completion of the present invention.

The inventors of the present invention have now prepared a PEG-conjugated EPO by reacting recombinant human EPO with a polyethylene glycol (PEG) derivative having an active ester at one end, such as a methoxy-PEG-succinimidyl lower fatty acid ester. This PEG-conjugated EPO comprises a composition of conjugates having 1 to 3 linear PEG molecules per rhEPO molecule. A mono-methoxy PEG-EPO (mono-mPEG-EPO) conjugate has one linear PEG molecule per rhEPO molecule, which is primarily attached to the ε-amino group of the lysine residue at position 52 of rhEPO. As further described below, the inventors of the present invention first confirmed that the PEG-conjugated EPO of the present invention had significantly sustained efficacy, as compared with unconjugated native EPO.

Further, the inventors of the present invention determined the apparent molecular weight of PEG-conjugated EPO by gel filtration column chromatography in an aqueous medium using globular proteins as molecular weight markers, as detailed in Example 2, for the purpose of predicting the in vivo apparent size behavior of PEG-conjugated EPO molecules. As a result, it was surprisingly found that PEG conjugates of native EPO rich in sugar chains had an apparent molecular weight exceeding 100 kDa, and more specifically that a PEG conjugate of native EPO prepared using 40 kDa branched PEG had an apparent molecular weight of approximately 800 kDa or more. In view of such a surprisingly high value of the apparent molecular weight focused here, along with the fact that receptor binding in native EPO was limited to exposed protein structural moieties because of abundant sugar chains on EPO, the inventors of the present invention concluded that PEG conjugation to native EPO should be optimized for efficacy by controlling the molecular weight and the number of PEG molecules used for conjugation.

Thus, the inventors of the present invention further prepared a mono-methoxy PEG-EPO (mono-mPEG-EPO) conjugate having one linear PEG molecule of 5 kDa, 10 kDa, 15 kDa, 20 kDa or 30 kDa per native EPO molecule, a di-methoxy PEG-EPO (di-mPEG-EPO) conjugate having two linear PEG molecules of 5 kDa, 10 kDa, 15 kDa, 20 kDa or 30 kDa per native EPO molecule, and a mono-branched methoxy PEG-EPO (mono-mPEG2-EPO) conjugate having one double-branched PEG molecule of 10 kDa, 20 kDa or 40 kDa per native EPO molecule. As further described in the Examples below, a comparison among these three types of PEG-conjugated EPO indicated that the plasma retention was longer in the di-methoxy PEG-EPO (di-mPEG-EPO) and mono-branched methoxy PEG-EPO (mono-mPEG2-EPO) conjugates than in the mono-methoxy PEG-EPO conjugate, whereas the in vivo erythropoietic effect was greater in the mono-methoxy PEG-EPO conjugate. This supported the above-mentioned inventors' view that there was an optimal range for PEG conjugation to native EPO.

BRIEF DESCRIPTION OF DRAWINGS

FIG. 10 graphically shows cell growth activity on EPO-dependent cells in the presence of PEG-conjugated EPOs, including the mono-mPEG10K-EPO, mono-mPEG15K-EPO and mono-mPEG20K-EPO conjugates according to the present invention.

FIG. 11 graphically shows cell growth activity on EPO-dependent cells in the presence of PEG-conjugated EPOs, including the mono-mPEG5K-EPO, mono-mPEG20K-EPO and mono-mPEG30K-EPO conjugates according to the present invention.

FIG. 12 graphically shows the time course of peripheral reticulocyte counts after administration of PEG-conjugated EPOs, including the mono-mPEG5K-EPO, mono-mPEG10K-EPO, mono-mPEG15K-EPO, mono-mPEG20K-EPO and mono-mPEG30K-EPO conjugates according to the present invention.

FIG. 13 graphically shows the time course of hemoglobin levels after administration of PEG-conjugated EPOs, including the mono-mPEG5K-EPO, mono-mPEG10K-EPO, mono-mPEG15K-EPO, mono-mPEG20K-EPO and mono-mPEG30K-EPO conjugates according to the present invention.

FIG. 14 graphically shows the AUC of peripheral reticulocyte counts after administration of PEG-conjugated EPOs, including the mono-mPEG5K-EPO, mono-mPEG10K-EPO, mono-mPEG15K-EPO, mono-mPEG20K-EPO and mono-mPEG30K-EPO conjugates according to the present invention.

PREFERRED MODE FOR CARRYING OUT THE INVENTION

Figure 1:
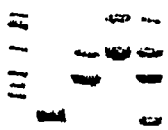
FIG. 1 shows an SDS-PAGE pattern of the PEG-conjugated EPOs (mono-mPEG-EPO and di-mPEG-EPO) prepared in the present invention, unconjugated EPO and others.

In view of the foregoing, for example, a highly purified mono-methoxy PEG-EPO (mono-mPEG-EPO) conjugate, which has a PEG molecule primarily attached to the amino group of the lysine residue at position 52 of native EPO, is desirable for use in formulating the PEG-conjugated EPO of the present invention into pharmaceuticals. It may also be possible to formulate the mono-methoxy PEG-EPO (mono-mPEG-EPO) conjugate as a main component, together with its activity-related byproducts generated during conjugation (e.g., a di-methoxy PEG-EPO (di-mPEG-EPO) conjugate).

EPO available for use in PEG conjugation of the present invention is intended to encompass commercially available recombinant human EPOs produced in animal host cells, as well as their variants modified to include substitution or deletion of one or more amino acids constituting these EPOs or modified to include addition of one or more amino acids.

In the present invention, any PEG derivative having one methoxylated end can be used for PEG conjugation. In addition, the other unmethoxylated end of such a PEG derivative may be converted into a succinimidyl lower fatty acid ester, preferably succinimidyl propionate or succinimidyl butyrate (SPA-PEG or SBA-PEG, respectively), for reaction with an amino group of EPO. These PEG derivatives can provide stable PEG conjugates because they have no ester moiety in their backbone, except for their end activated for reaction.

In order that native EPO binds to the EPO receptors on erythrocyte precursor cells and transmits signals driving differentiation of the cells into erythrocytes, the protein structural regions essential for this purpose should be exposed. However, in native EPO, the regions essential for receptor binding and signal transduction are localized in small exposed protein moieties because native EPO has a much higher sugar content than other recombinant pharmaceutical proteins. Thus, when conjugation, particularly with a polymer compound, occurs in such limited exposed protein moieties, the conjugation would reduce the EPO activity and ultimately fail to achieve the initial goal that sustained-action drugs are developed.

In the present invention, the inventors completed the invention by determining the desired molecular weight and site for PEG conjugation in order to provide native EPO under particular conditions, as mentioned above, with greater and more sustained in vivo efficacy than those of native EPO although the EPO activity was slightly affected at the receptor binding level.

Although native EPO contains several lysine residues as amino acid residues capable of PEG conjugation, particularly preferred is a PEG-conjugated EPO where PEG conjugation occurs on the amino group of the lysine residue at position 52. In one aspect, the present invention encompasses a composition of PEG-conjugated EPOs where PEG conjugation occurs primarily on the amino group of the lysine residue at position 52.

In this case, the PEG-conjugated EPO composition comprises a mono-PEG-conjugated EPO where PEG conjugation occurs on the amino group of the lysine residue at position 52. It may further comprise a mono-PEG-conjugated EPO having one PEG molecule on an amino acid residue at other position and/or a PEG-conjugated EPO where PEG conjugation occurs on two or more amino acid residues in native EPO.

The PEG-conjugated EPO contained in this composition preferably has one to three PEG molecules per EPO molecule, more preferably one PEG molecule per EPO molecule.

This PEG-conjugated EPO composition preferably comprises a mono-PEG-conjugated EPO where PEG conjugation occurs on the amino group of the lysine residue at position 52 as well as a mono-PEG-conjugated EPO having one PEG molecule on an amino acid residue at other position and/or a PEG-conjugated EPO where PEG conjugation occurs on two or more amino acid residues in native EPO.

The molecular weight of PEG used for conjugation can be changed as appropriate for the degree of sustained efficacy required by the resulting PEG-conjugated EPO, the degree of decreased EPO activity, etc. The molecular weight of one PEG molecule is 5 to 40 kDa, preferably 10 to 30 kDa, more preferably 20 to 30 kDa, and linear PEG is preferred to branched PEG if they have the same molecular weight. The apparent molecular weight of PEG-conjugated EPO in an aqueous medium is 100 to 900 kDa, preferably 150 to 650 kDa, more preferably 400 to 650 kDa, as measured by gel filtration column chromatography under the conditions described in Example 2.

PEG molecules used for conjugation preferably have the linear form, but it is possible to use branched or star-shaped PEG molecules as long as the apparent molecular weight of the resulting PEG-conjugated EPO is in the range mentioned above. In the case of branched or star-shaped PEG, PEG conjugation also occurs on the same amino acid residues as mentioned above.

Techniques for purification of PEG-conjugated EPO include PEG/dextran two-phase partition, gel filtration chromatography, ion-exchange chromatography, hydrophobic interaction chromatography, reverse phase chromatography and affinity chromatography.

With respect to the physiological activities and sustained efficacy of the PEG-conjugated EPOs prepared in the present invention, a comparison test was made for the following individual items between vehicle and PEG-conjugated EPOs, including unconjugated native EPO, di-methoxy PEG-EPO and mono-branched PEG-EPO, confirming that the PEG-conjugated EPOs of the present invention had greater and more sustained in vivo efficacy than unconjugated native EPO. Further, the greatest and most sustained in vivo efficacy was confirmed in a mono-methoxy PEG-EPO conjugate with an apparent molecular weight of 400 to 650 kDa (see Examples 2 and 9) where PEG conjugation occurred primarily on the amino group of the lysine residue at position 52 using linear PEG of 20 to 30 kDa.

More specifically, unconjugated native EPO and the PEG-conjugated EPOs of the present invention were tested for their plasma retention in rats after a single tail vein injection, indicating that longer plasma retention was provided by a PEG-conjugated EPO having a larger number of higher molecular weight PEG molecules and having a higher apparent molecular weight, as normally expected.

On the other hand, the PEG-conjugated EPOs were assayed for their in vitro cell growth activity on EPO-dependent cells (BaF/EpoR cells), indicating that the PEG-conjugated EPOs of the present invention still retained in vitro cell growth activity although they showed some decrease in the activity as compared with unconjugated native EPO. This suggests that PEG conjugation affects the binding affinity to the receptor, but does not completely block the region directly binding to the receptor. Among the PEG-conjugated EPOs of the present invention, mono-methoxy PEG-EPO showed much higher activity than the other PEG-conjugated EPOs (see Example 4).

Further, an in vivo test was performed on rats to monitor changes in reticulocyte counts and hemoglobin levels after a single tail vein injection of unconjugated native EPO or each PEG-conjugated EPO of the present invention, confirming that the PEG-conjugated EPOs of the present invention produced good results in both reticulocyte counts and hemoglobin levels. Unlike common PEG-conjugated proteins, the PEG-conjugated EPO of the present invention has been confirmed to produce extremely good results, particularly when PEG conjugation occurs primarily on the amino group of the lysine residue at position 52 using 10-30 kDa PEG to give a mono-methoxy PEG-EPO conjugate with an apparent molecular weight of 150 to 650 kDa, as shown in the data on reticulocyte counts and hemoglobin levels (see Examples 5 and 11).

The use of the PEG-conjugated EPOs (preferably, mono-methoxy PEG-EPO) according to the present invention allows an extended interval for erythropoietin administration. For example, the interval can be extended to once per week from 2-3 times per week or extended to every 10 days to every 2 weeks from every week. Therefore, it is possible not only to ease the physical and time burden on patients by reducing the numbers of hospital visits and painful injections, but also to save medical costs by reducing the load on medical staff members.

The dose will vary depending on and should be adjusted as appropriate for the cause and severity of anaemia, the age and erythropoietin sensitivity of individual patients, etc. For example, for once-a-week intravenous injection, the dose will be 1 to 100 µg, preferably 5 to 50 µg per adult.

The PEG-conjugated EPO of the present invention can be administered to patients by various routes such as intravenous injection, intravenous drip infusion, subcutaneous injection, transmucosal (e.g., transpulmonary, transnasal) application and percutaneous application.

Depending on the employed route of administration, the PEG-conjugated EPO of the present invention may be formulated into the desired dosage form such as solutions, lyophilized preparations, prefilled syringe-, painless needle- or needleless-systems for subcutaneous administration, or sustained release preparations for intracutaneous implantation (e.g., microcapsules, polymeric micelles, polymer-based gelatinous preparations, liposomes), resulting in EPO formulations more stable than native erythropoietin. Sustained release preparations of PEG-conjugated EPO are more advantageous than those of native erythropoietin, in that PEG conjugation stabilizes erythropoietin activity in the sustained release preparations and that PEG-conjugated erythropoietin shows much longer plasma retention than native erythropoietin.

EXAMPLES

The present invention will be further described in the following Examples, which are not intended to limit the scope of the invention.

Example 1

Preparation of PEG-Conjugated EPOs (1)

(Preparation of mono-mPEG-EPO and di-mPEG-EPO)

To a solution of rhEPO (in 100 mM phosphate buffer, pH 8.0), methoxy PEG-succinimidyl propionate (PEG Mw: about 20 kDa, Shearwater Polymers, Inc.) (hereinafter referred to as mPEG-SPA) was added and stirred at room temperature for 30 minutes. 1/10 volumes of a 100 mM glycine solution was added and stirred at room temperature for an additional 30 minutes to deactivate the active ester. Four reactions were carried out in the same manner as shown above. Table 1 shows the concentration and volume of the rhEPO solution and the molar ratio of added mPEG-SPA to rhEPO in each reaction. Each reaction solution was concentrated through a Centricon-50 (Millipore) simultaneously with replacement of the solvent by 20 mM phosphate buffer-150 mM NaCl (pH 7.4).

TABLE 1

Reactions of PEG-conjugated EPO

| | Reaction 1 | Reaction 2 | Reaction 3 | Reaction 4 |
|---|---|---|---|---|
| EPO concentration (mg/mL) | 2.94 | 1.75 | 2.81 | 2.45 |
| EPO volume (mL) | 0.50 | 2.31 | 2.50 | 2.04 |
| Molar ratio of mPEG-SPA (per mole of EPO) | 3.97 | 5.00 | 5.08 | 5.03 |

Each concentrated solution was purified by gel filtration on Superdex 200 HR 10/30 (Pharmacia Biotech) to collect both mono-mPEG-EPO and di-mPEG-EPO fractions, provided that the concentrated solution from Reaction 1 in Table 1 was used as such for purification, while the others were purified in 2 to 4 divided portions. In the case of Reactions 2 to 4, an intermediate fraction including mono-mPEG-EPO and di-mPEG-EPO, which was eluted as a mixture of both conjugates, was collected separately and purified again on Superdex 200 HR 10/30 to separate mono-mPEG-EPO and di-mPEG-EPO fractions. The fractions obtained through a series of purification steps were respectively combined for each conjugate to collect mono-mPEG-EPO (3.8 mg) and di-PEG-EPO (1.6 mg). Each of the collected mono-mPEG-EPO and di-mPEG-EPO was filtered through a 0.22 µm Milex filter (Millipore) to give sterilized di-mPEG-EPO (1.6 mg) and mono-mPEG-EPO (3.8 mg). These samples (about 0.75 mg/mL, 1 µL each loaded into a sample well of an electrophoretic gel) were SDS-PAGE electrophoresed on PastGel Gradient 4-15 (Pharmacia Biotech) and stained with PhastGel Blue R (Pharmacia Biotech) (see FIG. 1, in which EPO is intended to mean rhEPO).

In this example, rhEPO and PEG-conjugated EPOs were quantified based on their absorbance at a wavelength of 279 nm, given that a 1 mg/mL rhEPO solution had an absorbance of 0.93 at a wavelength of 279 nm (found in Biochemical Data Book). In other examples, quantification was performed, given that a 1 mg/mL rhEPO solution had an absorbance of 1.31 at 281 nm.

Example 2

Molecular Weight Determination of PEG-Conjugated EPOs (1)

(Molecular Weight Determination of Linear PEG-Conjugated EPOs)

To a solution of rhEPO (960 µL, 0.49 mg/mL in 100 mM phosphate buffer, pH 8.0), mPEG-SPA (5.32 mg, PEG Mw: about 20 kDa, mPEG-SPA/rhEPO=10.2 (mol/mol)) was added and stirred gently at room temperature for 1 hour. After addition of a 1M Gly solution (100 µL), the reaction solution was diluted in PBS (500 µL) and concentrated to 390 µL through a Centricon-50. The concentrated solution was applied to two Superose 6 HR 10/30 (1.0×30 cm, bed volume:

24 mL, Pharmacia Biotech) columns in series and eluted with PBS to collect both di- and mono-mPEG-EPO fractions.

Each of the resulting di- and mono-mPEG-EPO fractions was concentrated through a Centricon-50 simultaneously with replacement of the solvent by Milli-Q water. The molecular weight of each conjugate was then calibrated from BSA standards in ToF-MS analysis using sinapinic acid/50% MeCN (4.05 mg/405 µL) as a matrix and at a sample/matrix ratio of 5 µL/5 µL.

For use in molecular weight determination by gel filtration, each sample solution provided for ToF-MS analysis (30-35 µL) was diluted in PBS (200 µL), applied to two Superose 6 HR 10/30 (1.0×30 cm, bed volume: 24 mL, Pharmacia Biotech) columns in series and then eluted with PBS to measure the respective elution times of unconjugated rhEPO and di- and mono-mPEG-EPOs. A molecular weight calibration kit for gel filtration (Amersham Pharmacia Biotech) was used to prepare the following mixed standard solutions: (i) Thyroglobulin (Mw 669000), Aldolase (Mw 158000) and Chymotripsinogen A (Mw 25000) and (ii) Ferritin (Mw 440000) and Ovalbumin (Mw 43000), which were then subjected to gel filtration under the same conditions. A calibration curve was prepared from the elution times of individual standards and used to determine the respective molecular weights of rhEPO and di- and mono-mPEG-EPOs.

(Preparation and Molecular Weight Determination of Branched PEG-Conjugated EPOs)

To a solution of rhEPO (500 µL, 2.27 mg/mL in 100 mM phosphate buffer, pH 8.0), branched mPEG2-NHS (5.32 mg, PEG Mw: about 40 kDa (20 kDa×2), branched mPEG2-NHS/rhEPO=2.99 (mol/mol)) was added and stirred gently at room temperature for 30 minutes. After addition of a 1M Gly solution (50 µL, in 20 mM Tris.HCl, pH 8.0), stirring was continued at room temperature for an additional 30 minutes. The solvent was replaced by 20 mM Tris.HCl (pH 8.0) through a Centricon-50 and adjusted to a final volume of 750 µL. The resulting solution was applied to ion-exchange chromatography on Resourse Q (1 mL, Pharmacia Biotech) and eluted with a gradient of 0-50% Eluent B (pH 8.0, 20 mM Tris.HCl, 0.5 M NaCl) in Eluent A (pH 8.0, 20 mM Tris.HCl) to collect fractions containing branched PEG-conjugated EPOs, which were then concentrated to 375 µL through a Centricon-50. After addition of PBS (25 µL), the solution was applied to two Superose 6 HR 10/30 (1.0×30 cm, bed volume: 24 mL, Pharmacia Biotech) columns in series and then eluted with PBS to collect a di-mPEG2-EPO (di-branched mPEG-EPO) and tri-mPEG2-EPO (tri-branched mPEG-EPO) fraction as well as a mono-mPEG2-EPO (mono-branched mPEG-EPO) fraction. Each of the resulting two fractions was concentrated through a Centricon-50 simultaneously with replacement of the solvent by Milli-Q water. The molecular weight of each conjugate was then calibrated from BSA standards in ToF-MS analysis using sinapinic acid/50% MeCN (4.05 mg/405 µL) as a matrix and at a sample/matrix ratio of 5 µL/5 µL.

For use in molecular weight determination by gel filtration chromatography, each sample solution provided for ToF-MS analysis was diluted in PBS (200 µL for di-/tri-, 150 µL for mono-), applied to two Superose 6 HR 10/30 (1.0×30 cm, bed volume: 24 mL, Pharmacia Biotech) columns in series and then eluted with PBS to measure the respective elution times of unconjugated rhEPO and di- and mono-mPEG-EPOs. A molecular weight calibration kit for gel filtration (Amersham Pharmacia Biotech) was used to prepare the following mixed standard solutions: (i) Thyroglobulin (Mw 669000), Aldolase (Mw 158000) and Chymotripsinogen A (Mw 25000) and (ii) Ferritin (Mw 440000) and Ovalbumin (Mw 43000), which were then subjected to gel filtration chromatography under the same conditions. A calibration curve was prepared from the elution times of individual standards and used to determine the molecular weight of mono-mPEG2-EPO (mono-branched mPEG-EPO).

Table 2 shows the molecular weights of rhEPO, di- and mono-mPEG-EPO, and mono-mPEG2-EPO (mono-branched mPEG-EPO) (in the table, EPO, Linear and Branched are intended to mean rhEPO, linear and branched, respectively).

TABLE 2

Molecular weights of PEG-conjugated EPOs

| | | | Measured Mw (Da) | |
|---|---|---|---|---|
| | | Calculated Mw (Da) | ToF-MS | Gel filtration |
| | EPO | 29000[1] | 28400 | 70000 |
| Linear PEG | mono-mPEG-EPO | 50000 | 49800 | 402000 |
| | di-mPEG-EPO | 71000 | 71300 | 914000 |
| Branched PEG | mono-mPEG$_2$-EPO | 71000 | 71200 | 823000 |
| | di-mPEG$_2$-EPO | 113000 | 113000 | (2080000)[2] |

[1]putative molecular weight of EPOCH (chemical analysis) found in Journal of clinical therapeutics & medicine, Vol. 6, Suppl. 2 (May) 1990, p. 24
[2]out of calibration range (shown for reference)

Example 3

Identification of Sites for PEG Conjugation

The PEG-conjugated EPO (mono-mPEG-EPO) from Example 1 was analyzed to identify its site for PEG conjugation.

Figure 2:
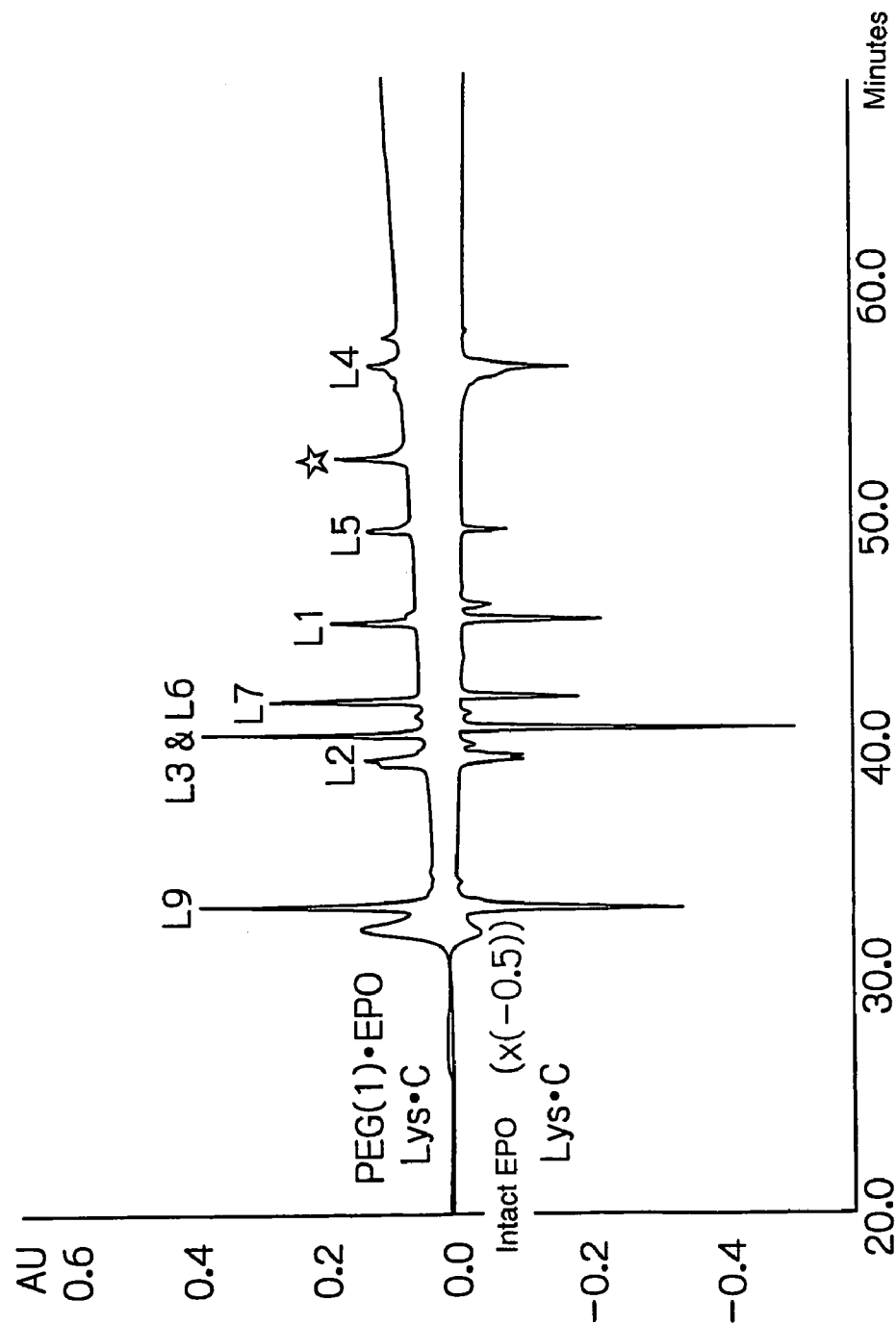
FIG. 2 shows a chromato pattern of the mono-mPEG-EPO conjugate according to the present invention, which is digested with endoprotease Lys-C and mapped by liquid chromatography.

Mono-mPEG-EPO (denoted as PEG(1)-EPO in FIG. 2) and unconjugated rhEPO (denoted as intact EPO in FIG. 2) were digested with endoprotease Lys-C, followed by peptide mapping on a RP/C18 column.

(Experimental Method)

Mono-mPEG-EPO (786 µg/mL, PEG Mw: about 20 kDa) and rhEPO (1 mg/mL) were used as samples.

a) Reduced Carboxymethylation (RCM) and Lys-C Digestion

A denaturing solution was 300 mM phosphate buffer (pH 8.0)/6M guanidine hydrochloride/6 mM EDTA. Five volumes of the denaturing solution were added to each sample (50 µg as EPO) to denature and reduce EPO overnight at room temperature in the presence of DTT (1.5 µmol, 50-fold more than Cys). After addition of monoiodoacetic acid (3.15 µmol, 2.1-fold more than DTT), the reaction mixture was carboxymethylated in the dark at room temperature for 45 minutes and then dialyzed against 50 mM Tris.HCl (pH 8.5). Digestion was carried out overnight at 37° C. in the presence of Lys-C (1 µg, substrate:enzyme=50:1), followed by addition of 1/10 volumes of 10% TFA for peptide mapping.

b) Peptide Mapping

A Vydac C18 (218TP52, 2.1 mm×250 mm) was used as a column and a SMART system (Pharmacia) was used for LC. The flow rate was set to 100 µL/minute and detection was performed at 220 nm and 280 nm. The solvent and gradient for elution were set as follows:

Solvent A: 0.1% TFA
Solvent B: 90% MeCN/0.1% TFA
Gradient: 5% B/15 min, 5-100% B/85 min, 100% B/10 min. FIG. 2 shows the chromato pattern obtained.

A comparison between mono-mPEG-EPO (denoted as PEG(1)-EPO in FIG. 2) and unconjugated rhEPO (denoted as intact EPO in FIG. 2) indicates a substantial loss of L4 and a significant decrease in L3 (L3 & L6 peak in FIG. 2). This suggests that PEG conjugation is more likely to occur on Lys52 at the boundary between L3 and L4. In addition, a new peak appears between L5 and L4, which may be relevant to a PEG-conjugated peptide. Further, in view of the fact that L4 does not completely disappear and L1 slightly decreases, there is a potential molecular species where PEG conjugation occurs at the N-terminal (Ala1) indicated by L1. The chromato pattern suggests that 70% to 80% of PEG conjugation occurs on Lys52.

Example 4

Assay for Cell Growth Activity of PEG-Conjugated EPOs on EPO-Dependent Cells (1)

Figure 3:
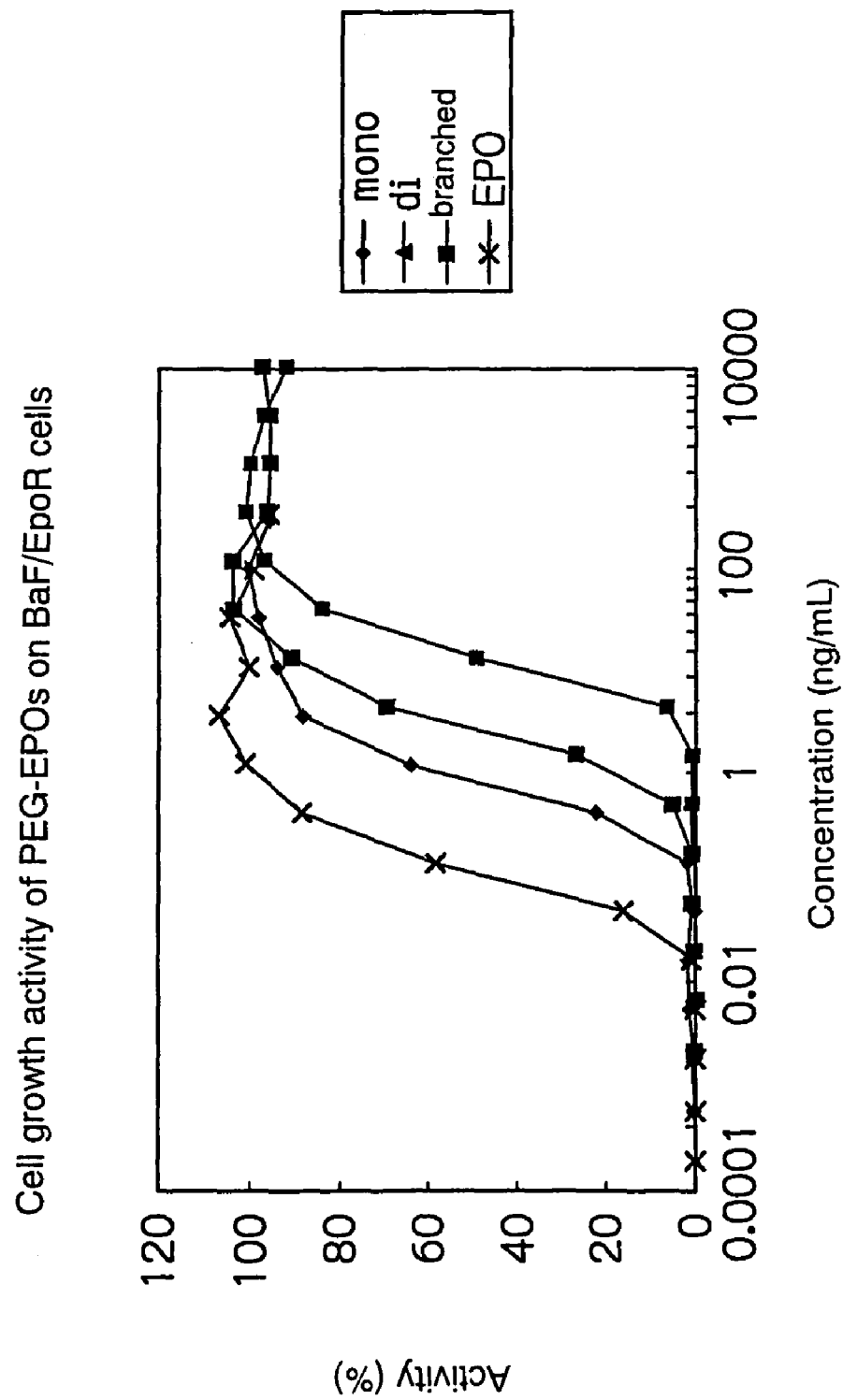
FIG. 3 graphically shows cell growth activity on EPO-dependent cells in the presence of PEG-conjugated EPOs, including the mono-mPEG-EPO conjugate according to the present invention.

BaF/EpoR cells showing EPO-dependent growth (Blood, 90, 1867-, 1997, PNAS, 93, 9471-, 1996) were washed by repeating 4 cycles of resuspension in 2% FCS-containing RPMI and centrifugation. The cells were then suspended in 10% FCS-containing RPMI at a density of $1 \times 10^6$ cells/10 mL and dispensed into each well of 96-well plates in a volume of 50 µL per well. Meanwhile, test samples were prepared using 10% FCS-containing RPMI as a diluent to give the respective dilution series of EPO as well as mono-mPEG-EPO, di-mPEG-EPO and mono-branched mPEG-EPO prepared in Examples 1 and 2. Each sample solution (50 µL/well, n=3) was added to and mixed with the BaF/EpoR cells in the 96-well plates, followed by incubation at 37° C. under a humidified atmosphere of 5% $CO_2$ for 24 hours. Each well was supplemented with 10 µL Cell Count Reagent SF (Nacalai Tesque, Inc.) and measured for its absorbance at wavelengths of 450 nm and 620 nm, which was defined as the value at time 0. The plates were allowed to stand at room temperature for an additional 6 hours, followed by measurement of absorbance at wavelengths of 450 nm and 620 nm to plot the data in graph form (see FIG. 3, in which mono, di, branched and Epo are intended to mean mono-mPEG-EPO, di-mPEG-EPO, mono-branched mPEG-EPO and rhEPO, respectively). Among the data obtained, 3 points showing a linear dose-response relationship were analyzed by linear regression to determine ED50 for each sample and its 95% confidence interval using a SAS program. The results are summarized in Table 3 (in which branched-mPEG-EPO denotes mono-branched mPEG-EPO).

TABLE 3

| Cell growth activity on EPO-dependent cells | | | |
|---|---|---|---|
| | ED50 (ng/mL) | 95% Confidence interval | Specific activity |
| rhEPO | 0.12 | 0.10-0.14 | 1.0 |
| mono-mPEG-EPO | 0.94 | 0.73-1.2 | 0.13 |
| di-mPEG-EPO | 15 | 13-18 | 0.0079 |
| branched mPEG-EPO | 3.0 | 2.4-3.8 | 0.040 |

Example 5

Assay for Sustained Efficacy of Mono-mPEG-EPO, di-mPEG-EPO and rhEPO

Mono-mPEG-EPO (786 µg/mL, having one mPEG molecule per rhEPO molecule) and di-mPEG-EPO (640 µg/mL, having two mPEG molecules per rhEPO molecule) prepared in Example 1 were used as test materials. Each of them was PEGylated by attaching approximately 20 kDa mPEG, which had been ester-activated at one end, to an amino group in rhEPO, followed by purification via gel filtration chromatography.

Each PEG-conjugated EPO or rhEPO was diluted to 12.5 µg/mL in physiological saline containing 0.05% rat serum albumin and 0.05% Tween 20. Administration of the medium (vehicle) alone was defined as a negative control. These administration solutions were prepared on the first day of administration. In this Example, Slc:SD male rats (Japan SLC, Inc) were provided for the experiment when 7 weeks old. On the day of test material administration, the rats were divided into 4 groups of 4 rats such that all groups had substantially the same erythrocyte count.

These 4 groups of 4 rats were set as follows: vehicle group, rhEPO group, mono-mPEG-EPO group and di-mPEG-EPO group. Each rat received a single tail vein injection of 2 mL/kg (sample concentration: 25 µg/kg).

On the first day of administration and 2, 4, 7, 10, 14, 17, 21, 25, 29, 32, 35 and 39 days after administration, each rat was fixed on a retainer under unanesthetized conditions and blood was sampled from a wound made by sticking an injection needle into the tail vein. Each blood sample was assayed for its reticulocyte count and hemoglobin level. The hemoglobin level was determined using a micro cell counter (Sysmex F-800, Toa Medical Electronics Co., Ltd.).

At individual time points, the hemoglobin level and reticulocyte count were compared between the vehicle group and the rhEPO, mono-mPEG-EPO or di-mPEG-EPO group by Dunnett's multiple comparison test at 5% significance level to verify the significance of differences in the mean values.

Figure 4:
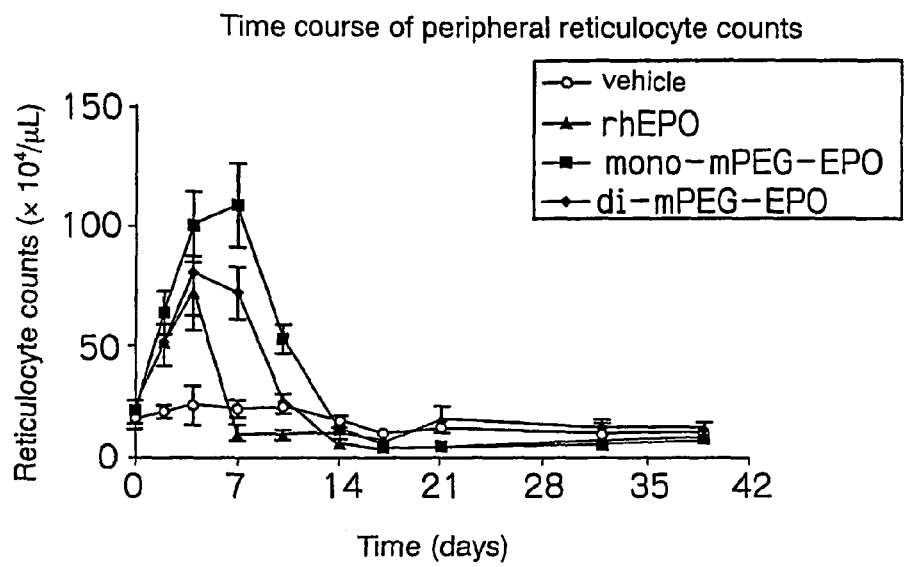
FIG. 4 graphically shows the time course of peripheral reticulocyte counts after administration of PEG-conjugated EPOs, including the mono-mPEG-EPO conjugate according to the present invention.
Figure 5:
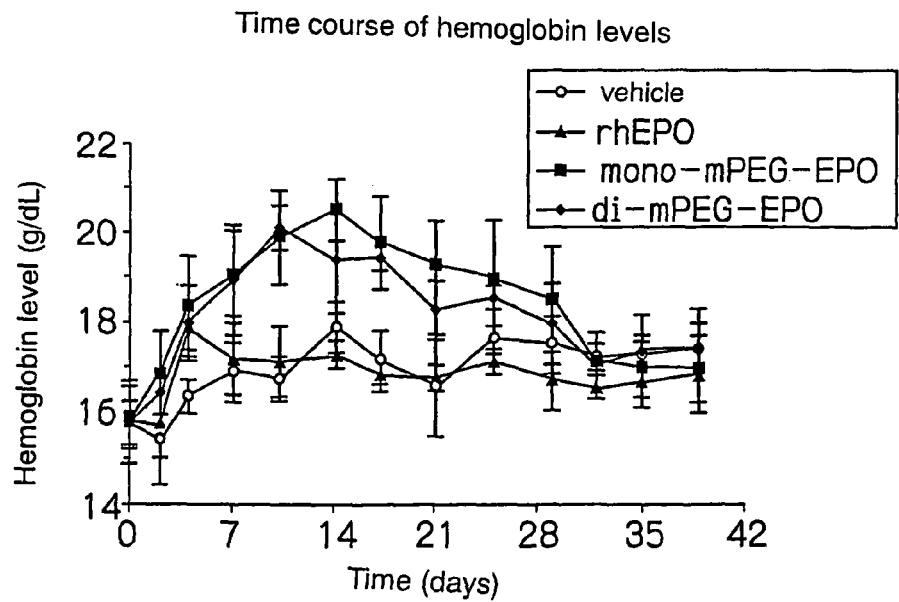
FIG. 5 graphically shows the time course of hemoglobin levels after administration of PEG-conjugated EPOs, including the mono-mPEG-EPO conjugate according to the present invention.

The results are shown in FIG. 4 (time course of peripheral reticulocyte counts) and FIG. 5 (time course of hemoglobin levels). In addition, the sustained period of erythropoiesis stimulation is summarized in Table 4.

TABLE 4

| Effective period of erythropoiesis stimulation induced by PEG-conjugated EPOs | |
|---|---|
| Test group | Effective period (days) as determined by hemoglobin level, >vehicle[a] |
| rhEPO | 1 (Day 4) |
| mono-mPEG-EPO | 22 (Day 4-25) |
| di-mPEG-EPO | 18 (Day 4-21) |

[a]significant difference from vehicle control ($P < 0.05$)

On Day 2 after administration, all the test groups showed significantly increased reticulocyte counts as compared with the vehicle group. In the rhEPO group, the reticulocyte count reached a peak on Day 4 after administration and decreased below the vehicle group on Day 7 after administration. In contrast, the mono-mPEG-EPO and di-mPEG-EPO groups showed a significantly higher value than the vehicle group by Day 10 and Day 7 after administration, respectively.

The hemoglobin level of the rhEPO group reached a peak on Day 4 after administration and decreased to substantially the same level as the vehicle group on Day 7 after administration. In contrast, the mono-mPEG-EPO and di-mPEG-EPO groups showed a peak on Day 14 and Day 10 after administration, respectively. These groups also showed a significantly higher level than the vehicle group by Day 25 and Day 21 after administration, respectively. The period, during which the test group showed a significantly higher level than the vehicle group, was only one day (Day 4) in the rhEPO group, whereas it was 22 days (Day 4-25) and 18 days (Day 4-21) in the mono-mPEG-EPO and di-mPEG-EPO groups, respectively (Table 4).

Example 6

Assay for Sustained Efficacy of Mono-mPEG-EPO, Mono-Branched mPEG-EPO and rhEPO

The same comparison experiment as shown in Example 5 was repeated, except for the following point. The erythropoietic effect was compared between the following conjugates when rats received a single tail vein injection of 5 or 1 μg/kg: mono-branched PEG-EPO (br-mPEG-EPO, having one branched PEG molecule) prepared through the reaction between an ester-activated (methoxy PEG 20000)$_2$ derivative of approximately 40 kDa ((mPEG)$_2$-succinimidyl propionate) and an amino group in rhEPO; and linear mono-PEG-EPO (mono-mPEG-EPO, having one linear PEG molecule) prepared through the reaction between an ester-activated mPEG derivative of approximately 20 kDa (mPEG-succinimidyl propionate) and an amino group in rhEPO. On the day of test material administration, rats were divided into groups of five such that all groups had substantially the same hemoglobin level.

On the first day of administration and 2, 4, 7, 10, 14, 21, 28 and 35 days after administration, each rat was fixed on a retainer under unanesthetized conditions and blood was sampled from a wound made by sticking an injection needle into the tail vein.

Figure 6:
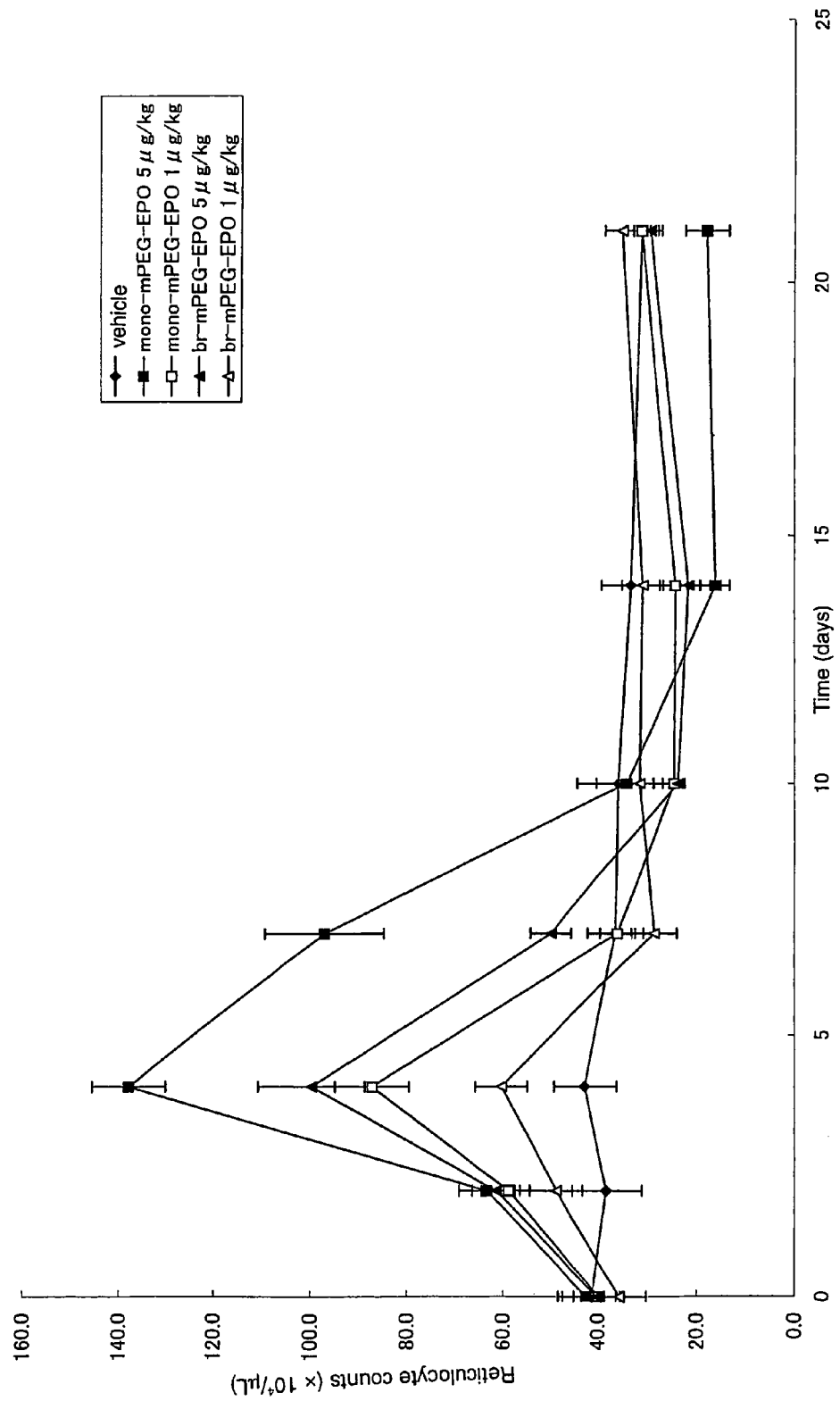
FIG. 6 graphically shows the time course of peripheral reticulocyte counts after administration of PEG-conjugated EPOs, including the mono-mPEG-EPO and mono-branched mPEG-EPO conjugates according to the present invention.
Figure 7:
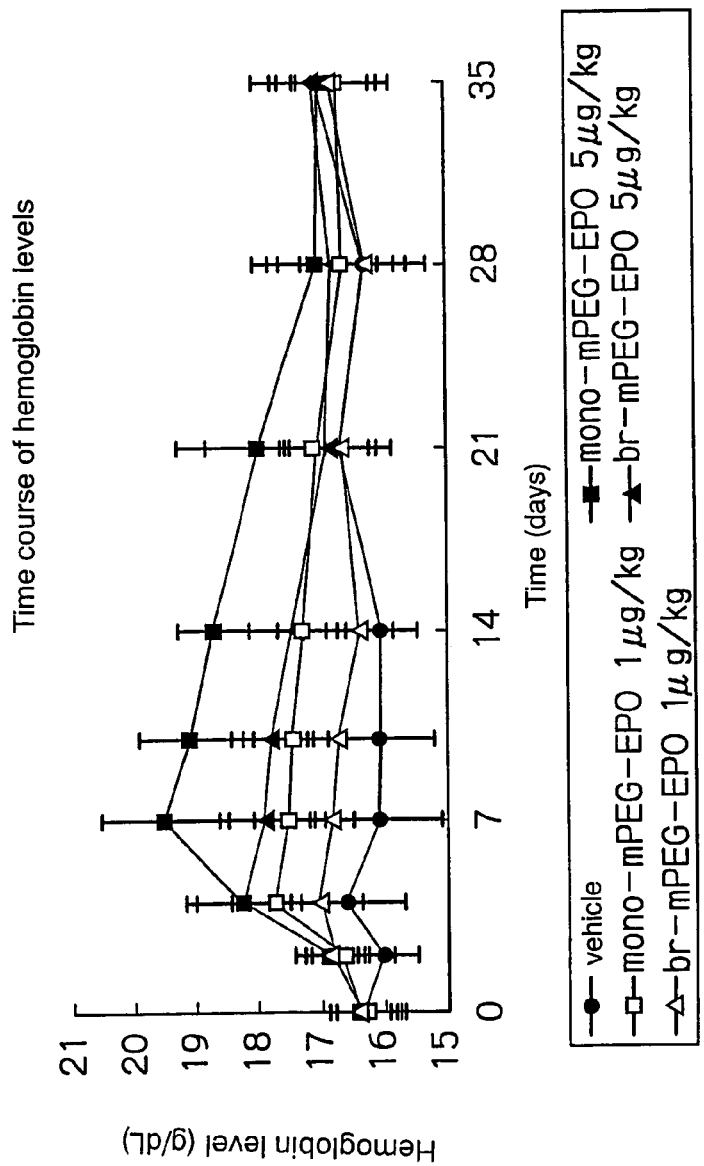
FIG. 7 graphically shows the time course of hemoglobin levels after administration of PEG-conjugated EPOs, including the mono-mPEG-EPO and mono-branched mPEG-EPO conjugates according to the present invention.

The results are shown in FIG. 6 (time course of peripheral reticulocyte counts) and FIG. 7 (time course of hemoglobin levels). In addition, the sustained period of erythropoiesis stimulation is summarized in Table 5. In FIGS. 6 and 7 and Table 5, br-mPEG-EPO denotes mono-branched mPEG-EPO.

TABLE 5

| Test group | Doses and sustained erythropoietic effect of PEG-conjugated EPOs |
|---|---|
| | Effective period (days) as determined by hemoglobin level, >vehicle[a] |
| mono-mPEG-EPO; 5 μg/kg | 13 (Day 2-14) |
| mono-mPEG-EPO; 1 μg/kg | 8 (Day 7-14) |
| br-mPEG-EPO; 5 μg/kg | 11 (Day 4-14) |
| br-mPEG-EPO; 1 μg/kg | —[b] |

[a]significant difference from vehicle control (P < 0.05)
[b]no significant difference from vehicle control On Day 2 after administration, all the test groups showed significantly increased reticulocyte counts as compared with the vehicle group, and a peak was observed on Day 4 after administration in each group. When peak reticulocyte count was compared among the test groups, the mono-mPEG-EPO (5 μg/kg) group was the highest of all, the mono-branched mPEG-EPO (5 μg/kg) group and the mono-mPEG-EPO (1 μg/kg) group were of the same level, and the mono-branched mPEG-EPO (1 μg/kg) group was the lowest. The period, during which the test group showed significantly higher reticulocyte counts than the vehicle group, was 6 days (Day 2-7) in the 5 μg/kg groups for both mono-mPEG-EPO and mono-branched mPEG-EPO, whereas it was 3 days (Day 2-4) in the 1 μg/kg groups (FIG. 6).

The hemoglobin level of the mono-mPEG-EPO (5 μg/kg) group reached a peak on Day 7 after administration, and the period, during which the group showed a significant increase over the vehicle group, was 13 days (Day 2-14). The mono-branched mPEG-EPO (5 μg/kg) group and the mono-mPEG-EPO (1 μg/kg) group both showed a peak on Day 4 after administration, and the period, during which the groups showed a significant increase over the vehicle group, was 11 days (Day 4-14) and 8 days (Day 7-14), respectively. In contrast, the mono-branched mPEG-EPO (1 μg/kg) group showed no significant difference from the vehicle group over the period of the experiment. (FIG. 7, Table 5).

Example 7

Dose-Dependent Efficacy of rhEPO and PEG-Conjugated EPO and Sustained Efficacy of PEG-Conjugated EPO Mono-mPEG-EPO prepared in Example 1 is verified for its efficacy at doses of 25 μg/kg or less, along with a comparison between single tail vein injection of mono-mPEG-EPO and continuous tail vein injection of unconjugated EPO.
(Dose-Dependent Efficacy of PEG-Conjugated EPO)

Mono-mPEG-EPO was examined for the time- and dose-dependency of its erythropoietic effect when 8-week-old male rats (n=5) received a single tail vein injection of the conjugate at doses of 25 μg/kg, 5 μg/kg, 1 μg/kg and 0.2 μg/kg.

Figure 8:
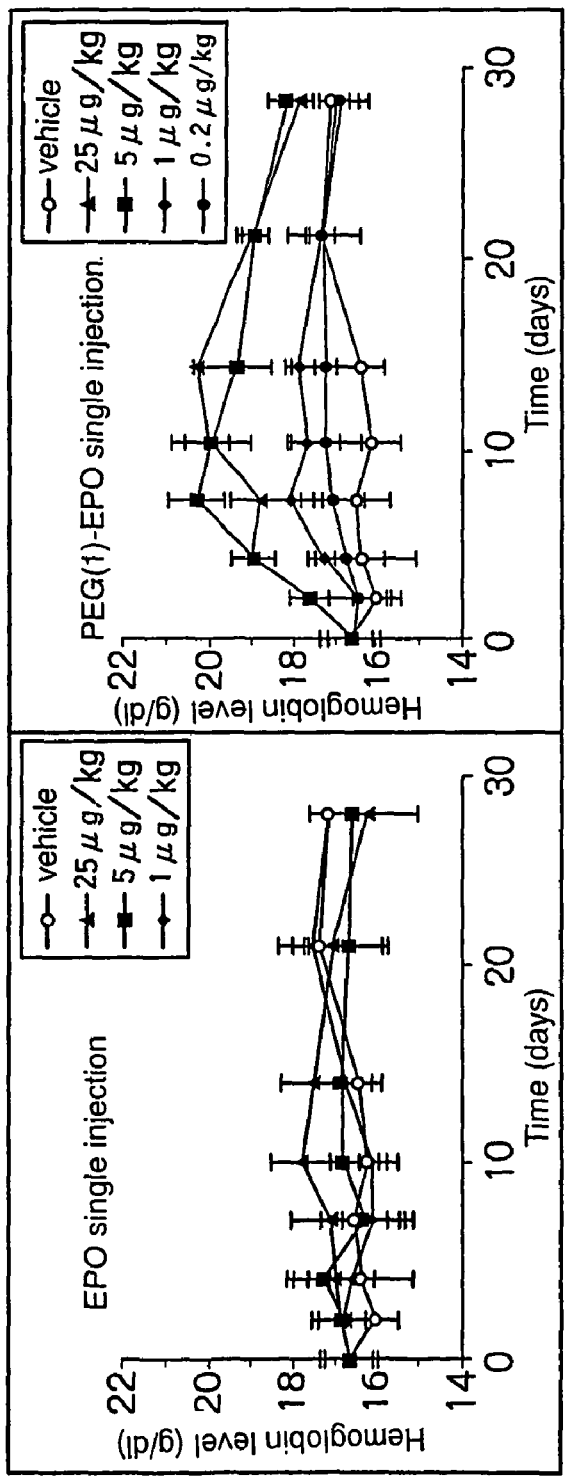
FIG. 8 graphically shows the dose-dependency of the mono-mPEG-EPO (PEG(1)-EPO) conjugate according to the present invention, as determined by its hemoglobin level.

FIG. 8 shows changes in hemoglobin levels of the rats which received a single tail vein injection of mono-mPEG-EPO at doses of 25 μg/kg, 5 μg/kg, 1 μg/kg and 0.2 μg/kg (in the figure, mono-mPEG-EPO is denoted as PEG(1)-EPO). When observed by Day 28 after administration, mono-mPEG-EPO was found to provide substantially the same peak hemoglobin level and sustained efficacy in the 25 μg/kg and 5 μg/kg groups, whereas the 1 μg/kg and 0.2 μg/kg groups were found to show dose-dependent decreases in peak hemoglobin level and sustained efficacy.
(Comparison of Efficacy Between Single Tail Vein Injection of Mono-mPEG-EPO and 5-Day Continuous Tail Vein Injection of rhEPO)

Figure 9:
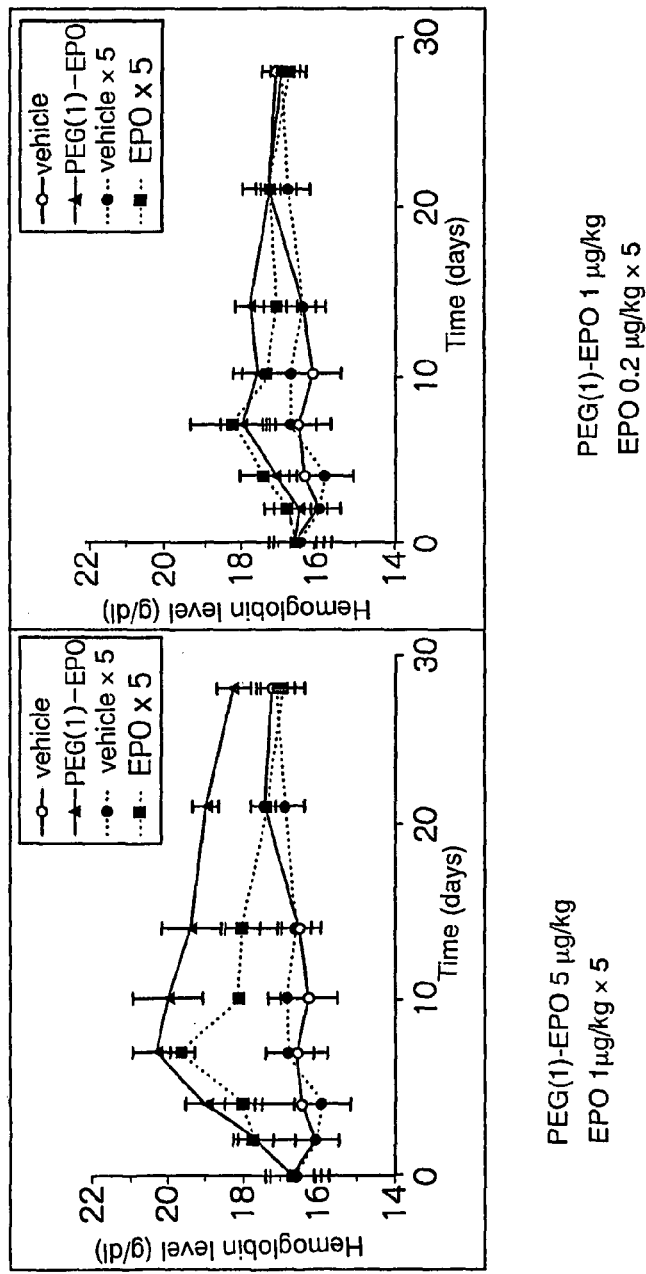
FIG. 9 graphically shows a comparison between 5-day continuous injection of EPO and single injection of the mono-mPEG-EPO (PEG(1)-EPO) conjugate according to the present invention.

A comparison of efficacy was made between single tail vein injection of mono-mPEG-EPO and 5-day continuous tail vein injection of rhEPO. FIG. 9 shows the results obtained (in the figure, mono-mPEG-EPO is denoted as PEG(1)-EPO). A comparison between single injection of mono-mPEG-EPO (5 μg/kg) and 5-day continuous injection of EPO (1 μg/kg per day, 5 μg/kg in total) indicated that the mono-mPEG-EPO group (5 μg/kg, single injection) showed a higher peak hemoglobin level and more sustained efficacy. In contrast, a comparison between single injection of mono-mPEG-EPO (1 μg/kg) and 5-day continuous injection of EPO (0.2 μg/kg per day, 1 μg/kg in total) indicated that both the groups showed substantially the same changes in hemoglobin levels. This strongly suggested that mono-mPEG-EPO could be administered with less frequency than rhEPO.

Example 8

Preparation of PEG-Conjugated EPOs (2)

(Preparation of mPEG5K-EPO)
EPO (1.3 mL, 2.27 mg/mL in 100 mM phosphate buffer, pH 8.0) was added to mPEG5K-SPA (3.38 mg, PEG/EPO=4.09 (mol/mol)) and stirred gently at room temperature for 30 minutes. After addition of a 1 M Gly solution in water (130 μL), stirring was continued at room temperature for an additional 30 minutes to deactivate active ester. The reaction solution was diluted in PBS (550 μL) and concentrated to 325

μL through a Centricon-50. After addition of PBS (150 μL), the solution was purified by gel filtration on two Superdex 200 HR 10/30 columns in series to collect three potential fractions predominantly rich in mono-mPEG5K-EPO, di-mPEG5K-EPO and a mixture thereof. Each fraction was concentrated through a Centricon-50 and subjected again to gel filtration under the same conditions to separate mono-mPEG5K-EPO and di-mPEG5K-EPO fractions, which were then respectively combined for each conjugate to give mono-mPEG5K-EPO (210 μg) and di-mPEG5K-EPO (218 μg). SDS-PAGE was performed to confirm the agreement of molecular weight between reaction products and collected samples.

(Preparation of mPEG10K-EPO, mPEG15K-EPO, mPEG30K-EPO, br-mPEG10K-EPO and br-mPEG20K-EPO)

Procedures for preparation will be shown below, with the details of reaction conditions ((i) to (iv)) being summarized in Table 6.

The indicated volume (ii) of an EPO solution (in 100 mM phosphate buffer, pH 8.0) at the indicated concentration (i) was added to the indicated volume (iii) of mPEG-SPA (linear) or br-mPEG-NHS (branched) at the indicated PEG/EPO ratio (iv), and they were stirred gently at room temperature for 30 minutes. After addition of 1/10 volumes (based on the EPO solution provided for the reaction) of a 1M Gly solution in water, stirring was continued at room temperature for an additional 30 minutes to deactivate active ester. The solvent was replaced by 20 mM Tris (pH 8.0) through a Centricon-50. The resulting solution was applied to ion-exchange chromatography on RESOURCE Q (1 mL) and eluted with a gradient of 0-100% of the same Eluent B as used in Example 2 to collect the respective fractions containing PEG-conjugated EPO and EPO, followed by replacement of the solvent by PBS through a Centricon-50. Each solution was subjected to gel filtration under the same conditions as described for preparation of mPEG5K-EPO, except that two Superose 6 HR 10/30 (1.0 cmφ×30 cm, Pharmacia Biotech) columns in series were used instead in the preparation of mPEG15K-EPO, mPEG30K-EPO and br-mPEG20K-EPO. Fractions which were expected to contain EPO conjugated with one or two mPEG or br-mPEG molecules were collected and concentrated. Fractions containing mixed mPEG-EPOs with different PEG conjugation patterns were concentrated again and then subjected to gel filtration to collect mono-mPEG-EPO and di-mPEG-EPO.

SDS-PAGE was performed to confirm the agreement of molecular weight between reaction products and collected samples. The yields of the resulting samples were as shown in Table 7.

TABLE 6

Reaction conditions for PEG-conjugated EPOs

| mPEG-SPA or br-mPEG-NHS | EPO concentration (i) (mg/mL) | EPO volume (ii) (mL) | mPEG-SPA or mPEG-NHS (iii) (mg) | PEG/EPO ratio (iv) (mol/mol) |
|---|---|---|---|---|
| Linear 10 kDa | 1.75 | 1.0 | 2.91 | 3.12 |
| Linear 15 kDa | 1.75 | 1.0 | 4.43 | 2.97 |
| Linear 30 kDa | 1.82 | 1.1 | 10.95 | 3.16 |
| Branched (br)10 kDa | 2.43 | 0.7 | 5.07 | 4.93 |
| Branched (br)20 kDa | 2.43 | 0.7 | 9.67 | 4.93 |

TABLE 7

Yields of PEG-conjugated EPOs

| | Yield (μg EPO) | |
|---|---|---|
| Type of PEG | mono-PEGylated | di-PEGylated |
| mPEG10K- | 257 | 146 |
| mPEG15K- | 277 | 135 |
| mPEG30K- | 300 | 167 |
| br-mPEG10K- | 247 | 138 |
| br-mPEG20K- | 265 | 150 |

Example 9

Molecular Weight Determination of PEG-Conjugated EPOs (2)

Various PEG-conjugated EPO solutions prepared in the same manner as shown in Example 8 (Preparation of PEG-conjugated EPOs) were concentrated through a Centricon-50 simultaneously with solvent replacement by Milli-Q water. MALDI-ToF-MS analysis was performed under the same conditions as shown in Example 2. Also, each sample residue provided for ToF-MS analysis was diluted in PBS and subjected to gel filtration under the same conditions as shown in Example 2. Under the same conditions as described for mPEG 10K- and mPEG15K- in Example 8, gel filtration column chromatography (GPC) was performed on each sample to measure its elution time.

In the case of mPEG30K-EPO, its concentrated solution was divided into two aliquots, one of which was provided for ToF-MS analysis and the other for GPC. In the case of br-mPEG10K-EPOs and br-mPEG20K-EPOs, the fraction at the elution time in GPC was collected and provided for MALDI-ToF-MS analysis after solvent replacement by Milli-Q water. Table 8 shows the results obtained.

TABLE 8

Molecular weights of PEG-conjugated EPOs

| | | Molecular weight (Da) | | |
|---|---|---|---|---|
| | Sample | Calculated | ToF-MS | GPC |
| PEG Linear PEG | EPO | 29000[1] | 28400 | 70000 |
| | mono-mPEG5000-EPO | 34100 | 33800 | 114000 |
| | di-mPEG5000-EPO | 39200 | 38900 | 161000 |
| | mono-mPEG20000-EPO | 50000 | 49800 | 402000 |
| | di-mPEG20000-EPO | 71000 | 71300 | 914000 |
| | mono-mPEG30000-EPO | 60500 | 59900 | 606000 |
| | di-mPEG30000-EPO | 92000 | 93000 | (1620000)[2] |
| Branched PEG | mono-br-mPEG10000-EPO | 39600 | 39600 | 161000 |
| | di-br-mPEG10000-EPO | 50200 | 50300 | 267000 |
| | mono-br-mPEG20000-EPO | 50000 | 49700 | 316000 |
| | di-br-mPEG20000-EPO | 71000 | 71500 | 649000 |
| | mono-br-mPEG40000-EPO | 71000 | 71200 | 823000 |
| | di-br-mPEG40000-EPO | 113000 | 113000 | (2080000)[2] |

[1] putative molecular weight of EPOCH (chemical analysis) found in Journal of clinical therapeutics & medicine, Vol. 6, Suppl. 2 (May) 1990, p. 24
[2] out of calibration range (shown for reference)

Example 10

Assay for Cell Growth Activity of PEG-Conjugated EPOs on EPO-Dependent Cells (2)

BaF/EpoR cells showing EPO-dependent growth (Blood, 90, 1867-, 1997, PNAS, 93, 9471-, 1996) were washed by repeating 2 cycles of resuspension in 1% FCS-containing RPMI and centrifugation. The cells were then suspended in 10% FCS-containing RPMI at a density of $1 \times 10^5$ cells/20 mL and dispensed into each well of 96-well plates in a volume of 50 µL per well. Meanwhile, test samples were prepared using 10% FCS-containing RPMI as a diluent to give the respective dilution series of EPO and mono-mPEG-EPOs. Each sample solution (50 µL/well, n=3) was added to and mixed with the BaF/EpoR cells in the 96-well plates, followed by incubation at 37° C. under a humidified atmosphere of 5% $CO_2$ for 24 hours. Each well was supplemented with 10 µL Cell Count Reagent SF (Nacalai Tesque, Inc.) and measured for its absorbance at wavelengths of 450 nm and 620 nm, which was defined as the value at time 0. The plates were allowed to stand at room temperature for an additional 5 hours, followed by measurement of absorbance at wavelengths of 450 nm and 620 nm to plot the data in graph form (see FIGS. 10 and 11, in which mono and Epo are intended to mean mono-mPEG-EPO and rhEPO, respectively). Among the data obtained, 2 points sandwiching the 50% activity point in the dose-response relationship were analyzed by linear regression to determine ED50 for each sample. The results are summarized in Tables 9 and 10.

TABLE 9

|  | ED50(ng/mL) | vs EPO(%) |
|---|---|---|
| EPO | 0.134 | 100.0 |
| mono-mPEG10000 | 0.255 | 52.5 |
| mono-mPEG15000 | 0.240 | 55.6 |
| mono-mPEG20000 | 0.557 | 24.0 |

TABLE 10

|  | ED50 (ng/mL) |
|---|---|
| mono-mPEG5000 | 0.158 |
| mono-mPEG30000 | 0.348 |
| mono-mPEG20000 | 0.374 |
| EPO | 0.072 |

Example 11

Assay for Sustained Efficacy of Mono-mPEG-EPOs with Different Molecular Weights Each PEG-conjugated EPO or rhEPO was diluted to 2.5 µg/mL in physiological saline containing 0.05% rat serum albumin and 0.05% Tween 20. Administration of the medium (vehicle) alone was defined as a negative control. These administration solutions were prepared on the first day of administration. In this Example, Slc:SD male rats (Japan SLC, Inc) were provided for the experiment when 7-8 weeks old. On the day of test material administration, the rats were divided into 7 groups of 5 rats such that all groups had substantially the same erythrocyte count.

These 7 groups of 5 rats were set as follows: vehicle group, rhEPO group, mono-mPEG5K-EPO group, mono-mPEG10K-EPO group, mono-mPEG15K-EPO group, mono-mPEG20K-EPO group and mono-mPEG30K-EPO group. Each rat received a single tail vein injection of 2 mL/kg (sample concentration: 5 µg/kg).

On the first day of administration and 2, 4, 5, 7, 10, 15, 21, 29 and 35 days after administration, each rat was fixed on a retainer under unanesthetized conditions and blood was sampled from a wound made by sticking an injection needle into the tail vein. Each blood sample was assayed for its reticulocyte count and hemoglobin level. The hemoglobin level was determined using a micro cell counter (Sysmex F-800, Toa Medical Electronics Co., Ltd.).

Further, as an efficacy indicator reflecting both an increase in reticulocyte counts and a period during which the increase was observed, the AUC of reticulocyte counts (Reti-AUC) by Day 15 after administration was calculated using the trapezoidal rule for each group.

The results are shown in FIG. 12 (time course of peripheral reticulocyte counts), FIG. 13 (time course of hemoglobin levels) and FIG. 14 (AUC of reticulocyte counts).

INDUSTRIAL APPLICABILITY

In order to achieve more sustained efficacy without losing physiological activities of native EPO, a glycoprotein rich in sugar chains, there was developed a PEG-conjugated EPO with significantly sustained efficacy, prepared by introducing a controlled number of PEG molecules at controlled positions. The ability of this PEG-conjugated EPO to provide more sustained efficacy without affecting erythropoietic effect inherent to native EPO allows, for example, a significant decrease in the number of administrations to patients, a decrease in pain associated with administration to patients, a decrease in the physical and time burden on diseased patients by reducing the number of hospital visits, as well as decreases in the load and hours on overworked medical staff members, including doctors, nurses and pharmacists, who work under extremely harsh conditions. Therefore, the PEG-conjugated EPO achieves medical cost savings in all aspects.

What is claimed is:

1. An isolated mono-methoxy polyethylene glycol-erythropoietin (mono-mPEG-EPO) conjugate, consisting of a native human erythropoietin (native EPO) which is chemically conjugated, at only the amino group of the lysine residue at position 52 of the native EPO, with a single linear polyethylene glycol (PEG) derivative having an active ester at one end (PEG-ester), so that the mono-mPEG-EPO conjugate has only one linear PEG molecule per native EPO molecule.

2. The mono-mPEG-EPO conjugate of claim 1 in the form of a sustained-action EPO formulation, wherein said PEG derivative having an active ester at one end is a methoxyl-PEG-succinimidyl lower fatty acid ester.

3. The mono-mPEG-EPO conjugate of claim 1 in the form of a sustained-action EPO formulation, wherein said PEG of said polyethylene glycol derivative is a linear PEG of molecular weight of 10-30 kDa.

4. The mono-mPEG-EPO conjugate of claim 3 in the form of a sustained-action EPO formulation, wherein said mono-mPEG-EPO conjugate is in an aqueous medium and wherein the apparent molecular weight of said mono-mPEG-EPO is 150-650 kDa, as measured by gel filtration column chromatography.

5. The mono-mPEG-EPO conjugate of claim 4 in the form of a sustained-action EPO formulation, wherein said apparent molecular weight is 400-650 kDa.

* * * * *